(12) United States Patent
Prabhakarpandian et al.

(10) Patent No.: US 10,775,364 B2
(45) Date of Patent: Sep. 15, 2020

(54) SYNTHETIC MICROFLUIDIC SYSTEMS FOR HYPOXIA

(71) Applicant: CFD Research Corporation, Huntsville, AL (US)

(72) Inventors: Balabhaskar Prabhakarpandian, Madison, AL (US); Kapil Pant, Madison, AL (US)

(73) Assignee: CFD Research Corporation, Huntsville, AL (US)

(*) Notice: Subject to any disclaimer, the term of this patent is extended or adjusted under 35 U.S.C. 154(b) by 398 days.

(21) Appl. No.: 15/017,125

(22) Filed: Feb. 5, 2016

(65) Prior Publication Data

US 2016/0153970 A1  Jun. 2, 2016

Related U.S. Application Data

(62) Division of application No. 14/202,491, filed on Mar. 10, 2014, now abandoned.

(60) Provisional application No. 61/775,158, filed on Mar. 8, 2013.

(51) Int. Cl.
*G01N 33/50* (2006.01)
*G01N 33/86* (2006.01)
*B01L 3/00* (2006.01)

(52) U.S. Cl.
CPC ..... *G01N 33/5029* (2013.01); *G01N 33/5005* (2013.01); *G01N 33/5011* (2013.01); *G01N 33/5061* (2013.01); *G01N 33/5088* (2013.01); *G01N 33/86* (2013.01); *B01L 3/5027* (2013.01); *G01N 2333/4703* (2013.01); *G01N 2333/70525* (2013.01)

(58) Field of Classification Search
CPC ........... G01N 33/5029; G01N 33/5061; G01N 33/5011; G01N 33/5005; G01N 33/5088; G01N 33/86; G01N 2333/70525; G01N 2333/4703; B01L 3/5027
USPC ................................ 435/7.1, 7.21, 29, 289.1
See application file for complete search history.

(56) References Cited

U.S. PATENT DOCUMENTS

| 6,846,641 B2 * | 1/2005 | Wieloch | G01N 33/5008 435/325 |
| 8,380,443 B2 | 2/2013 | Prabhakarpandian et al. | |
| 8,355,876 B2 | 5/2013 | Prabhakarpandian et al. | |

(Continued)

OTHER PUBLICATIONS

Yang, et al., An In Vitro Model of Ischemic Stroke, Methods in Molecular Biology, vol. 814, pp. 451-466 (2012).

*Primary Examiner* — Liban M Hassan
(74) *Attorney, Agent, or Firm* — Maschoff Brennan; Jonathan M. Benns (57) ABSTRACT

A method of inducing ischemia includes: providing a cell culture device having a first cell culture in an internal chamber and a second cell culture in at least one fluid channel and a perfusion modulating system that causes changes in oxygen flow in the internal chamber and/or at least one fluid channel; flowing liquid media having oxygen through the internal chamber and at least one fluid channel of the cell culture device; modulating oxygen perfusion in the internal chamber with the perfusion modulating system by varying and selectively blocking the flow rate of at least one of the liquid media or oxygen through the internal chamber to induce varying levels of ischemia; and assaying for ischemia in the first cell culture.

19 Claims, 8 Drawing Sheets

(56) References Cited

U.S. PATENT DOCUMENTS

| | | | |
|---|---|---|---|
| 2006/0258000 A1* | 11/2006 | Allen | C12M 41/34 |
| | | | 435/325 |
| 2010/0112690 A1* | 5/2010 | Eddington | C12M 23/12 |
| | | | 435/374 |
| 2011/0104658 A1 | 5/2011 | Prabhakarpandian et al. | |
| 2013/0149735 A1 | 6/2013 | Prabhakarpandian et al. | |
| 2014/0255971 A1 | 9/2014 | Prabhakarpandian et al. | |

* cited by examiner

SYNTHETIC MICROFLUIDIC SYSTEMS FOR HYPOXIA

CROSS-REFERENCE

This patent application is a divisional of Ser. No. 14/202,491 filed Mar. 10, 2014, which claims priority to U.S. Provisional Patent Application No. 61/775,158 filed on Mar. 8, 2013, and which applications is are both incorporated herein by specific reference in their entirety.

BACKGROUND

Ischemia and hypoxia are common in several pathological conditions, such as cancer, stroke, acute renal failure, and myocardial infarction. Myocardial infarction occurs when the blood supply from a coronary artery is occluded leading to reduced supply (e.g., ischemia) that results in hypoxia to portions of the myocardium. This blockage of the blood flow and oxygen supply is primarily due to an atherosclerosis plaque leading to partial or complete occlusion of the vessel and subsequent myocardial ischemia. Total occlusion of the vessel for more than 4-6 hours results in irreversible myocardial necrosis, but reperfusion within this period can salvage the myocardium and reduce morbidity and mortality. Following an ischemic attack, a series of response mechanisms in the heart, neural, hormonal systems, and vasculature are activated which though initially for beneficial purposes can contribute to worsening of the symptoms and eventual death.

Most of the models of in vivo myocardial ischemia use rodents. In the most commonly used experimental model, the left anterior descending coronary artery commonly called as LADA is ligated. This causes reduction in blood flow and subsequent ischemia. Fluorescent imaging is then used to visualize the vessels. For example, CD31 staining is used to visualize anatomic vessels and DiOC7 is used to visualize perfusion. Finally tissue hypoxia is quantified with EF5, a nitroheterocyclic compound that has been shown to form adducts at a much higher rate in hypoxic tissue. Even though the animal experiments provide detailed representation following ischemia, these experiments are expensive, technically complex and need to overcome ethical concerns.

In this regard, in vitro models were developed to study the effect of ischemia on cultured cardiomyocytes. These models range from treating cells to oxygen deprived media, elevated carbon dioxide levels, reduced nutrient media (absence of serum, etc.), and finally waste accumulation. Common methods rely on altering the cellular metabolism with a chemical agent (e.g., cyanide, azide, Antimycin A, etc.) or altering the external cellular environment by changing gas compositions which is achieved by changes in temperature and rate of change of fresh media. Currently, ischemia studies on myocytes cultured in vitro use one of the following two methods. In the first method, myocytes are cultured in a 35 mm Petri dish. When the cells are nearing confluency, a round glass coverslip is placed over part of the myocyte monolayer surface to restrict nutrient supply and gas diffusion. This rapidly decreases intracellular pH and produces three distinct zones within the monolayer called the ischemic zone (e.g., where the cells don't have access to fresh media and waste metabolites are present in excess), the border zone (e.g., partial cells experience excess waste metabolites and hypoxia whereas the other half of cells are viable), and finally the non-ischemic zone, where the cells have abundant supply of fresh nutrients. A less popular method called the picochamber system can be used to study ischemic conditions on a single cell where the cellular microenvironment oxygen is altered by an argon stream parallel to the surface.

However, all of these models have limitations. Therefore, it would be advantageous to have devices and methods that provide for improved experimental analysis and studies on cells and cultures under ischemic and hypoxic conditions.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes a microfluidic device and assay for studying ischemia and hypoxia on cells in controlled perfusion conditions. The microfluidic device can induce ischemia and hypoxia by interrupting the flow of media and oxygen to cells in the microfluidic device. The device can selectively block the flow of oxygen or fluids having oxygen from the cells in the device, which simulates blocking blood vessels supplying oxygen to tissue to provide a hypoxic condition. The resulting restriction of flow causes an oxygen shortage in the cells in the device, which can lead to necrosis in portions of the cells, cell culture, or tissue area in the device. The device can be used for a controlled study of ischemia and hypoxia and the impact on cells in the device, which can be extrapolated for understanding ischemia and hypoxia. The device can also be used for development of new therapeutics for treating ischemia and hypoxia affected tissues in a subject.

The device can be configured for high throughput assays used for studying any cell having ischemia or hypoxia. The device can have physiological realistic features, such as tissue chambers and vessel flow paths, which is referred to as a synthetic microvascular network (SMN). The device can have idealistic features, such as straight flow paths and regular shaped tissue chambers, which is referred to as an idealized microvascular network. SMN and IMN are known terms in the art. For example, the device can provide a platform for studying myocardial ischemia (MI) in a physiological microenvironment (e.g., SMN environment). MI occurs when the blood supply to portions of the heart is interrupted, which can be simulated by interrupting the flow of cell culture media, oxygen or oxygen-containing fluid to the cells in the device. The device may include means for inhibiting the supply of media and/or oxygen to the cells. For example, the device can be used to simulate blockage of a coronary artery following the rupture of an atherosclerotic plaque. The reduced flow of media (e.g., simulated blood supply) can simulate ischemia, and the nutrient shortage can lead to myocardial necrosis, which can cause contractile dysfunction and hinder the ability of the heart to perfuse vital organs necessary for survival. The same technique can be used to inhibit oxygen and induce hypoxia. The example presented here is based on myocytes. However, the device can use other cells to study ischemia and hypoxia in other tissues e.g., neurons, nephrons, or hepatocytes.

The device can be configured to provide an in vitro model to reproduce as many anatomical, physiological and biochemical aspects as possible of the in vivo features, in order to be functional and accurate. As such, the device can include a microenvironment with a central chamber having myocytes surrounded by a network of capillary channels in the device for providing nutrients to the central chamber. The shape of the central chamber and capillary network can be shaped similar to anatomical examples, which can be irregular and non-linear and referred to as synthetic microvascular networks (SMN). Alternatively, the shape of the central chamber and capillary network can be shaped in an idealized format with straight channels with regular and linear features, which is referred to as an idealized microvascular network (IMN). As such, the microfluidic device can be configured to mimic the microenvironment of tissue cells in a complex network of capillaries. Fluid flow (e.g., simulated blood flow and/or oxygen flow) in these capillary channels surrounding the central chamber can be readily switched on and off to simulate ischemia induced conditions and hypoxia. Cultured endothelial cells in the capillaries surrounding the central chamber (e.g., myocyte culture) enable studies on interaction between endothelial cells and tissue (e.g., myocardium). However, other cells can be used besides myocytes for studying other tissue types.

Figure 1A:
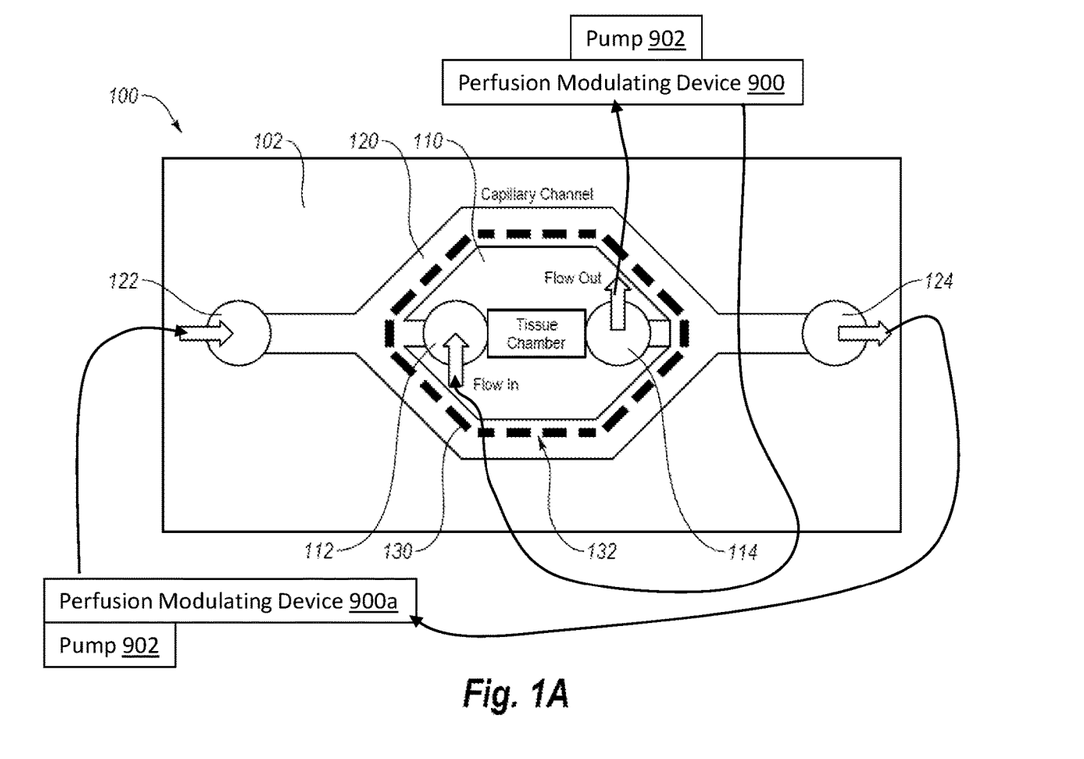
FIG. 1A illustrates an embodiment of a device for use in ischemia and hypoxia assays.
Figure 1B:
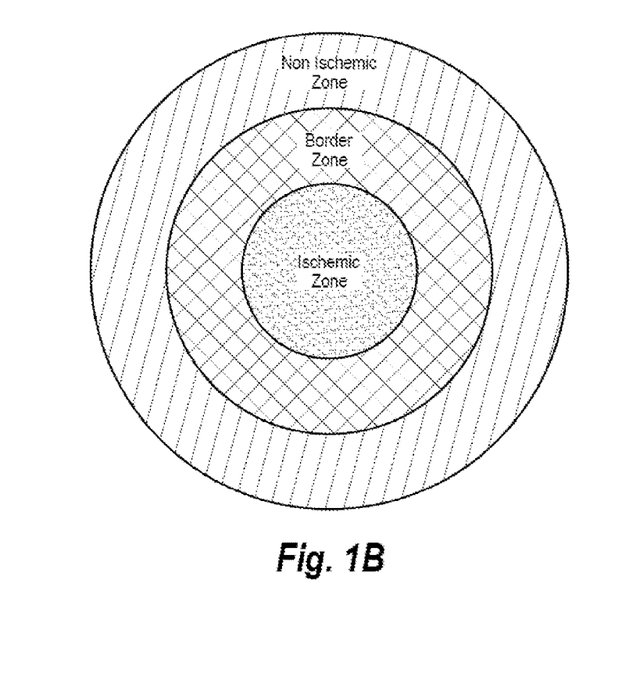
FIG. 1B illustrates a representation of ischemia zones in the central chamber of the device.

FIG. 1A illustrates an embodiment of a microfluidic device 100 in accordance with the present invention. As shown, the device includes a body 102 that defines an internal chamber 110 surrounded by a capillary channel 120. The internal chamber has a flow inlet 112 and a flow outlet 114. The capillary channel 120 has a capillary inlet 122 and a capillary outlet 124. The internal chamber 110 and capillary channel 120 are separated by posts 130 with gaps 132 between the posts 130.

The capillary channel 120 can be a fluid flow channel and the internal chamber 110 can be a tissue space. The capillary channel 120 and internal chamber can be linear elements or idealized (IMN) or non-linear elements or synthetic (SMN). FIG. 1A illustrates an IMN.

Figure 2A:
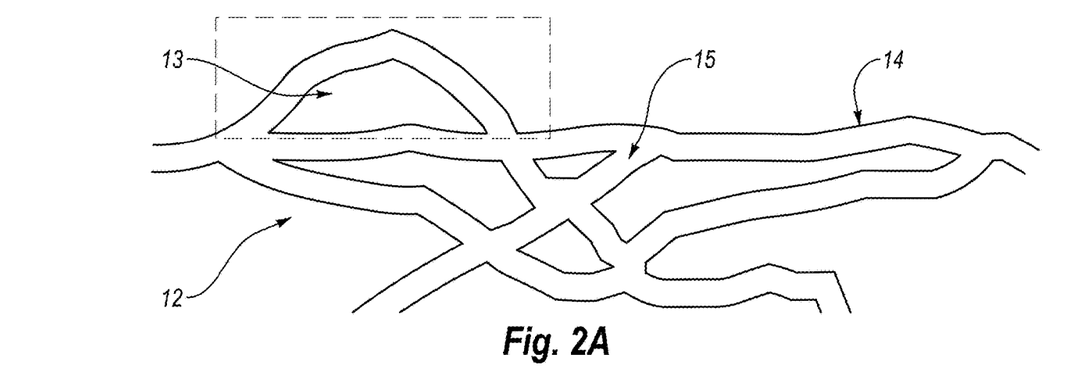
FIG. 2A illustrates an embodiment of a device having a central chamber and fluid channels that are modeled from physiological features.
Figure 2B:
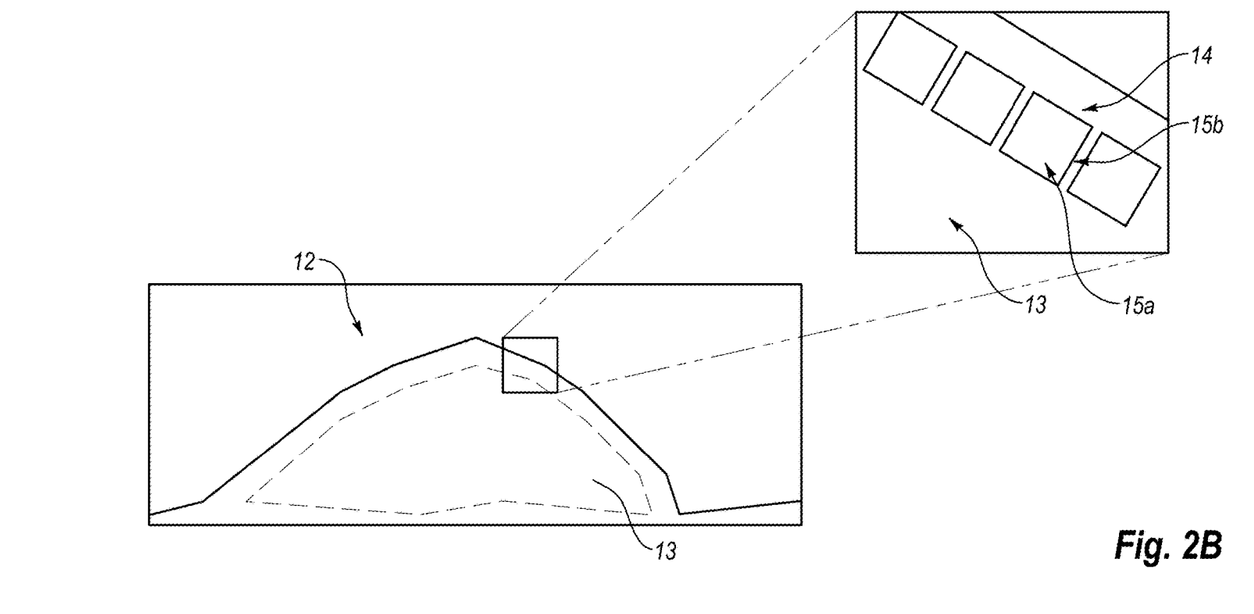
FIG. 2B illustrates a magnification of a wall separating the central chamber and fluid channels.

One embodiment of a synthetic microvascular network (SMN) 12 can include realistic flow paths and tissue spaces, as shown in FIG. 2A-2B. The capillary network is irregular. Here, the wall of a flow channel (e.g., capillary channel) separating the flow channel lumen from the lumen of the tissue space 13 is shown in detail to show the pillars 15a and gaps 15b. In this embodiment, one wall of the nonlinear flow channel 14 is constructed such that portions of the wall contain gaps 15b located between portions of the wall, called pillars 15a (or posts, islands, etc.), which may be configured to provide gaps 15b of various selected sizes. For fabrication of the SMN 12 comprising the extravascular (extra-flow channel) tissue space 13, CAD drawings of a physiological network are modified to include gaps 15b with desired gaps or pores in the walls of the vessels. The patterns of these vessels include tissue sections comprising a portion of or the entire physiological tissue space. The lumens of the tissue spaces shown in FIG. 2A and 2B may comprise posts, pillars, or other structures made of plastic substrate to facilitate the growth of adhesion-dependent cells.

Figure 2C:
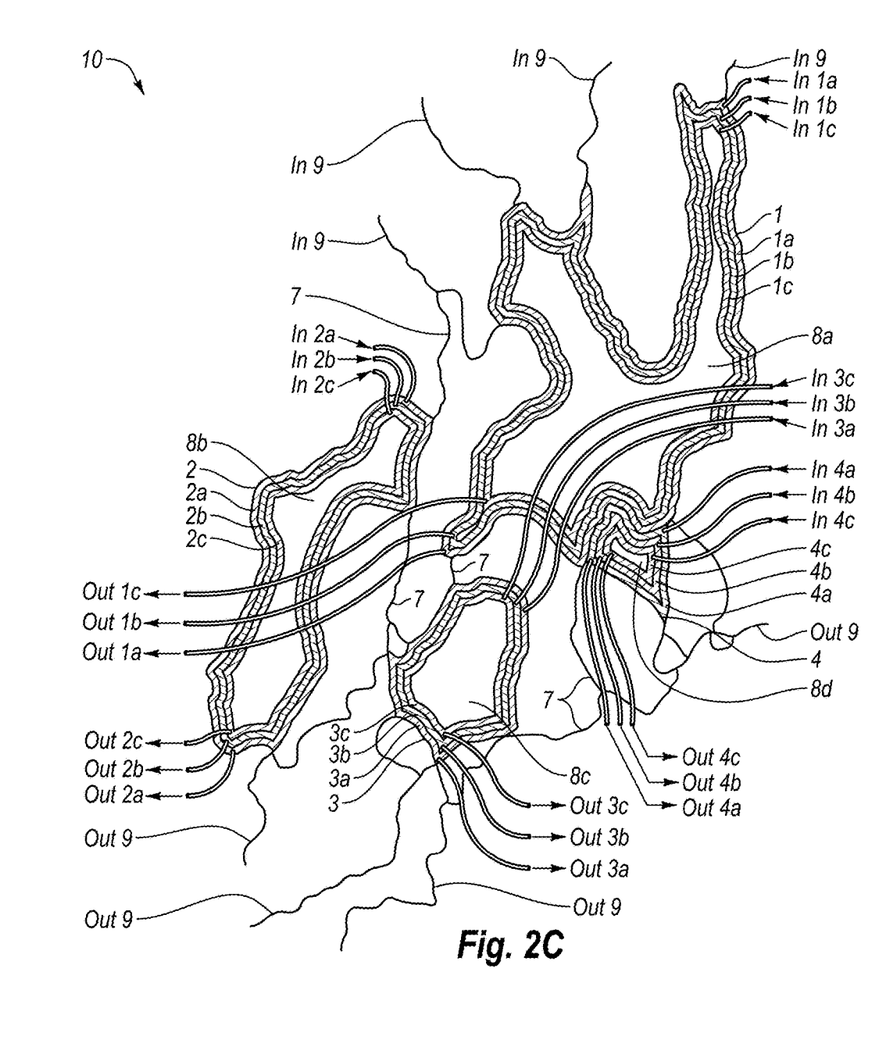
FIG. 2C illustrates an embodiment of a device having multiple channels.
Figure 6:
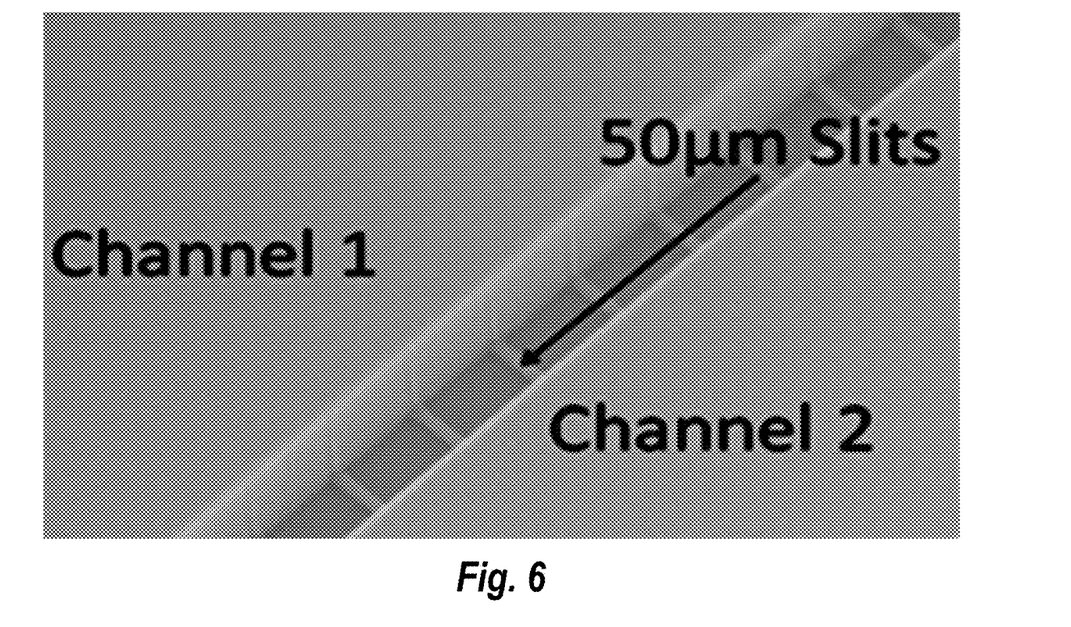
FIG. 6 illustrates an embodiment of a wall with slits that can separate two different channels in the device.

FIG. 6 shows that two capillary channels can be separated by a wall having 50 micron-wide slits. As such, the devices can include central chambers surrounded by at least two adjacent capillary channels. In view of the SMN of FIGS. 2A and 2B, a corresponding SMN modeled after live physiology with at least two capillary channels would look like FIG. 2C. FIG. 2C illustrates an embodiment of SMN network having SMN fluid pathways and SMN multi-chambered cell culture constructs.

FIG. 2C illustrates a SMN 10 having one of more fluid inlets In 9 and one or more fluid outlets Out 9 with one or more multi-channel constructs 1, 2, 3, 4, each having a central chamber 8a, 8b, 8c, 8d (e.g., while four multi-chamber constructs are shown, any integer can be used). The multi-chamber constructs 1, 2, 3, 4 can be configured with inlets and outlets in accordance with any of the embodiments or figures described herein. Also, while shown to be SMN, the configuration can be an IMN. The SMN can be configured with any number of fluid pathways 7 linking the multi-channel constructs, which can be in any manner, and which SMN can be designed via simulation of real biological or artificial fluid pathways.

As shown, multi-channel construct 1 can include a central chamber 8a surrounded by an outer conduit layer 1a (e.g., outer capillary channel) with barrier layer channels 1b, 1c therebetween. The outer conduit layer 1a can be fluidly coupled with an inlet In 9 and an outlet Out 9. Also, the outer conduit layer 1a can include an inlet In 1a and an outlet Out 1a. The barrier layer channels 1b, 1c, can include inlets In 1b, 1n 1c and outlets Out 1b, Out 1c, respectively. While not shown, the central chamber 8a can include inlets or outlets, or it can receive content from the barrier layer channel 1c.

As shown, multi-channel construct 2 can include a central chamber 8b surrounded by an outer conduit layer 2a (e.g., capillary channel) with barrier layer channels 2b, 2c therebetween. The outer conduit layer 2a can be fluidly coupled with an inlet In 9 and an outlet Out 9. Also, the outer conduit layer 2a can include an inlet In 2a and an outlet Out 2a. The barrier layer channels 2b, 2c, can include inlets In 2b, In 2c and outlets Out 2b, Out 2c, respectively. While not shown, the central chamber 8b can include inlets or outlets, or it can receive content from the barrier layer channel 2c.

As shown, multi-channel construct 3 can include a central chamber 8c surrounded by an outer conduit layer 3a (e.g., outer capillary channel) with barrier layer channels 3b, 3c therebetween. The outer conduit layer 3a can be fluidly coupled with an inlet In 9 and an outlet Out 9. Also, the outer conduit layer 3a can include an inlet In 3a and an outlet Out 3a. The barrier layer channels 3b, 3c, can include inlets In 3b, In 3c and outlets Out 3b, Out 3c, respectively. While not shown, the central chamber 8a can include inlets or outlets, or it can receive content from the barrier layer channel 3c.

As shown, multi-channel construct 4 can include a central chamber 8d surrounded by an outer conduit layer 4a with barrier layer channels 4b, 4c therebetween. The outer conduit layer 4a can be fluidly coupled with an inlet In 9 and an outlet Out 9. Also, the outer conduit layer 4a can include an inlet In 4a and an outlet Out 4a. The barrier layer channels 4b, 4c, can include inlets In 4b, In 4c and outlets Out 4b, Out 4c, respectively. While not shown, the central chamber 8d can include inlets or outlets, or it can receive content from the barrier layer channel 4c.

Figure 3A:
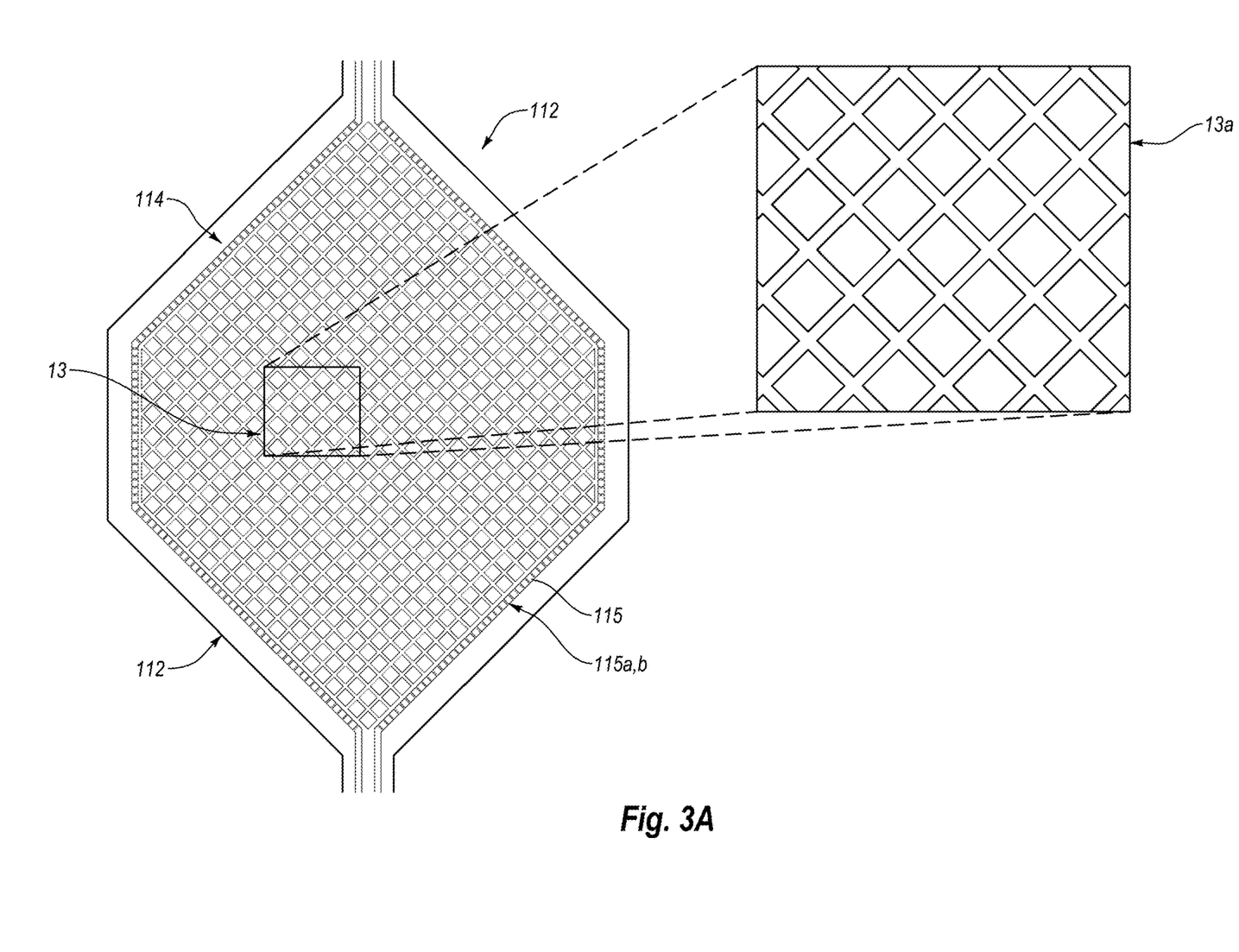
FIG. 3A illustrates an embodiment of an idealized device having a central chamber and fluid channels that are idealized.

FIG. 3A shows a portion of an idealized microvascular network IMN 112 in a microfluidic chip. The IMN 112 comprises the idealized extravascular tissue space 13 surrounded by linear flow channels 114. Walls 115 separating the tissue space 13 from the linear flow channels 114 are permeable to aqueous buffers and are formed by plastic structures 115b separated by gaps 115a that range in size from 0.2 μm to 5 μm. Alternatively, the walls 115 may be made liquid permeable by way of pores in the wall that are from 0.2 μm to 30 μm in diameter. The extravascular tissue space 13 contains posts 13a (e.g., pillars) configured to facilitate the growth of adhesion-dependent cells to form a three-dimensional solid mono- or co-tissue culture or tumor. The posts 13a can be included in any vascular fluid flow path or extravascular space in any of the microfluidic chips. The posts 13a distribution, amount or arrangement or shape. Also, the tissue space 13 can be devoid of the posts 13a.

Figure 3B:
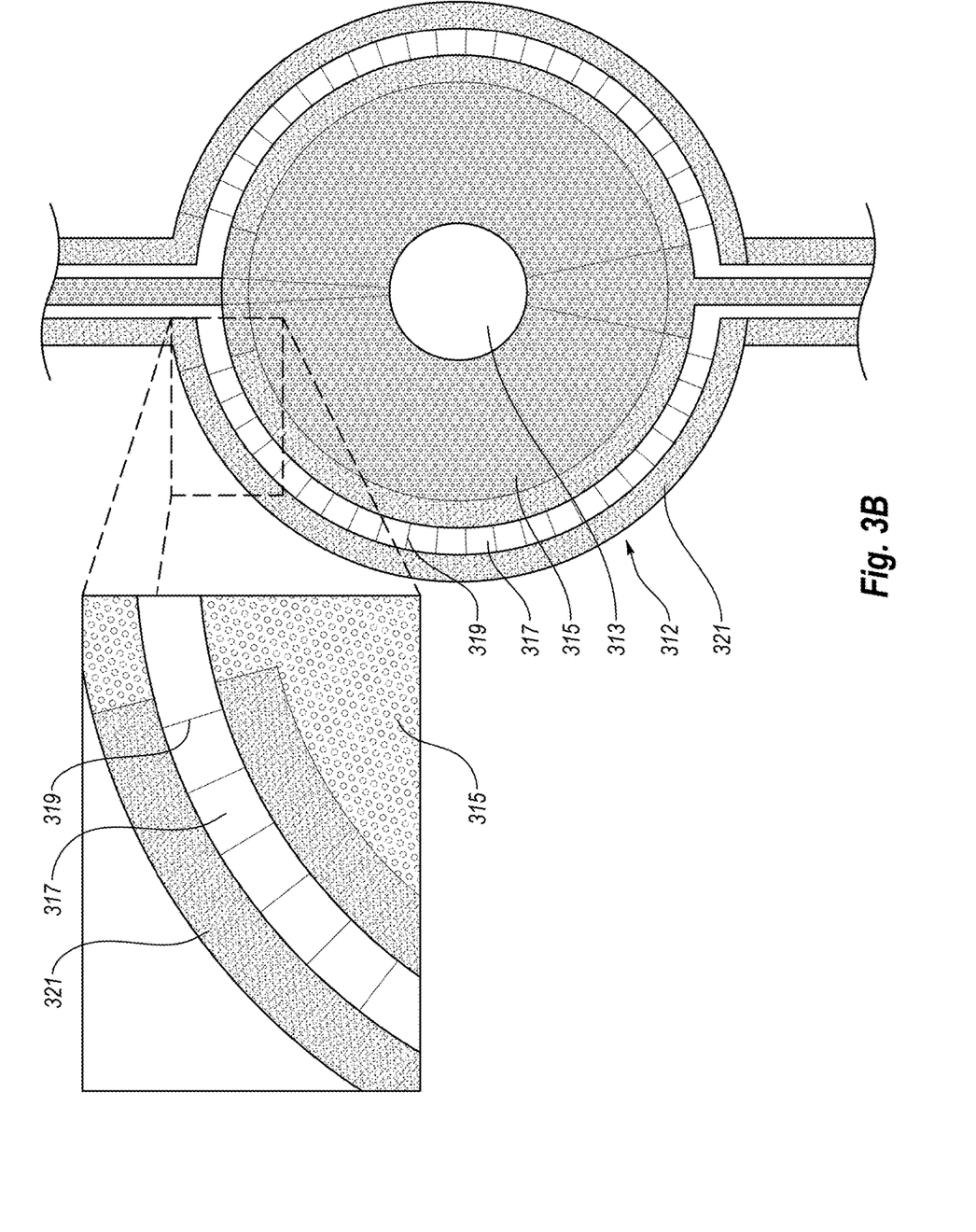
FIG. 3B illustrates an embodiment of a circular device having a central chamber and fluid channels that are idealized.

FIG. 3B shows a round IMN 312 in a microfluidic chip. The IMN includes a round tissue space 313 surrounded by a barrier space 315, which is surrounded by a wall 317 having gaps 319, and where an outer capillary channel 321 is on the outside. As shown, the barrier space 315 can include posts or pillars for cell culturing tissue.

The embodiments of the device can include a plastic, disposable and optically clear microfluidic chip containing two distinct sections. The first section includes a central chamber for culture of tissue cells surrounded by the second section being capillaries of endothelial cells. The device can be created by separating the central chamber (e.g., tissue chamber or internal chamber) for culture of cells (e.g., myocytes) from the capillary channels lined with endothelial cells by utilizing posts that mimic membranes. The posts create islands which are separated by submicron-micron gaps to allow for diffusion based fluidic connection between the capillary channels and the central chamber leading to a microenvironment observed in vivo with cells (e.g., myocytes) being surrounded by capillaries.

Figure 5:
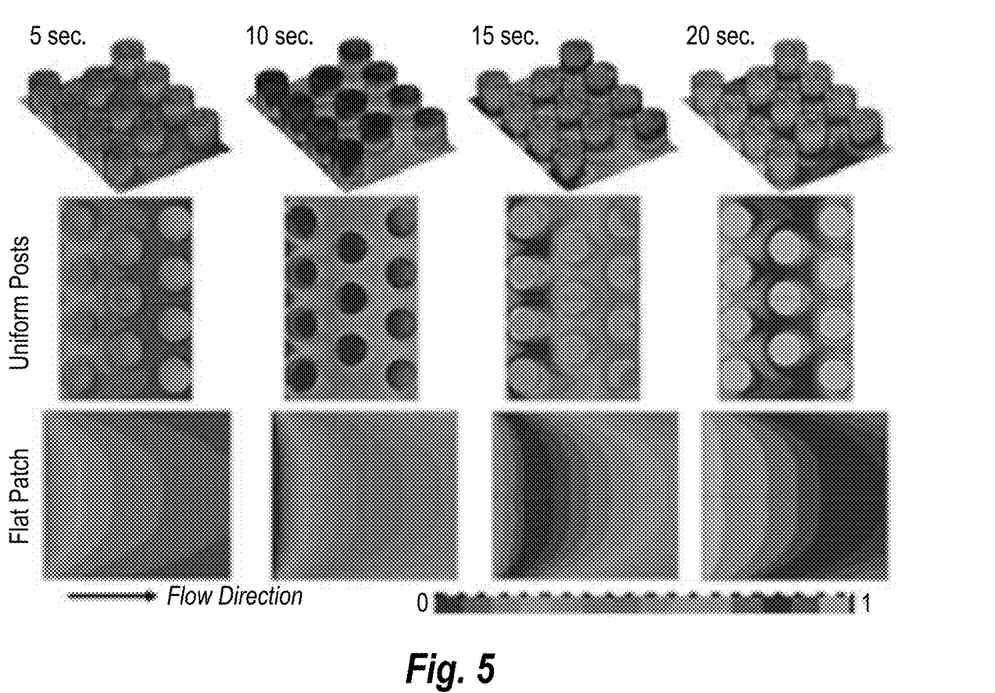
FIG. 5 illustrates fluid flow dynamics with posts that can be used as walls between the chamber and channels.

FIG. 5 shows that multiple pillars be used in the flow direction, which is from the capillary channels into the central chamber. As such, the walls can be a series of pillars with gaps and flow space therebetween.

Figure 3C:
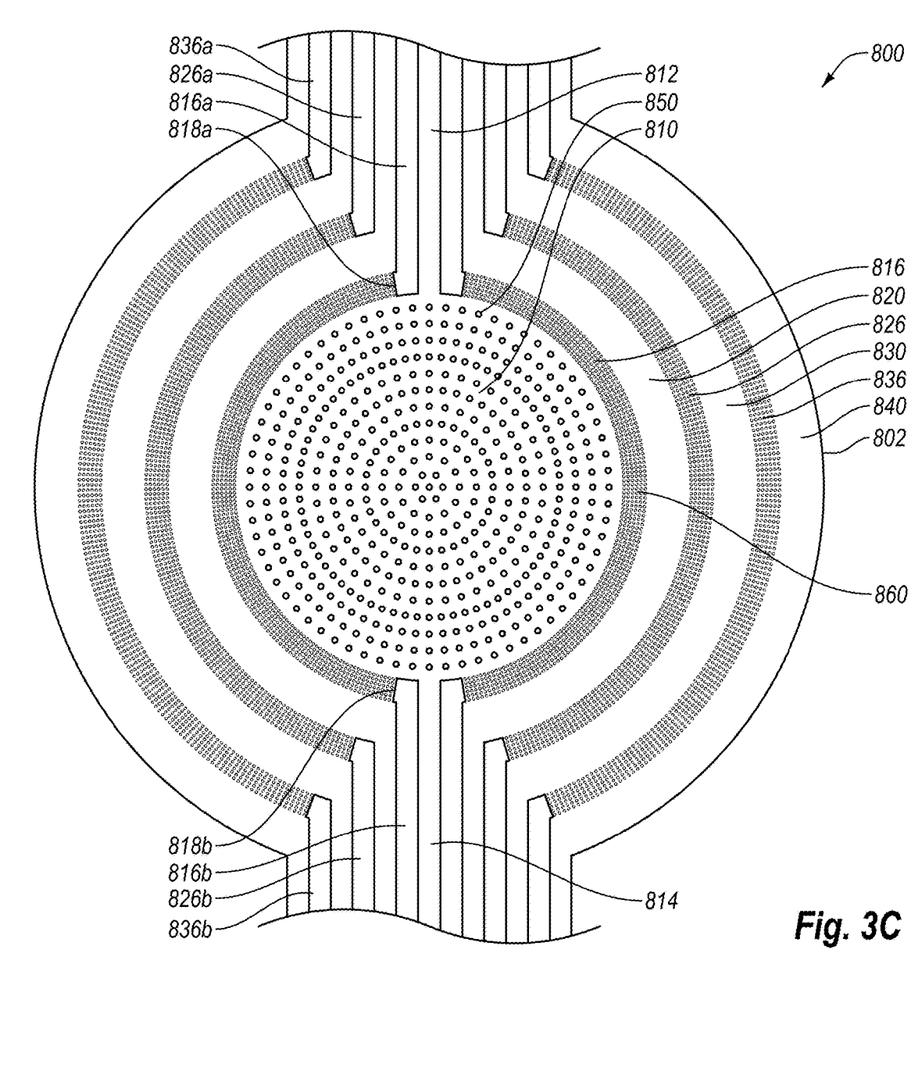
FIG. 3C illustrates an embodiment of a circular device having a central chamber and multiple fluid channels that are idealized.

FIG. 3C shows another embodiment of a multi-channel structure 800 in accordance with the principles of the present invention. Here, the walls are made of the series of pillars in accordance with FIG. 5. The multi-channel cell culture device 800 is shown to include an internal chamber 810, an inner boundary layer channel 820, an outer boundary layer channel 830, and an outer conduit layer channel 840. However, only one boundary layer channel or more than two additional boundary layer channel can be located between the internal chamber 810 and outer conduit layer channel 840. The internal chamber 810 can include a fluid inlet 812 and a fluid outlet 814. The inner boundary layer channel 820 can include at least one fluid inlet and at least one fluid outlet as described herein. The outer boundary layer channel 830 can include at least one fluid inlet and at least one fluid outlet as described herein. The outer conduit layer channel 840 can include at least one fluid inlet and at least one fluid outlet as described herein. The internal chamber 810 can be defined by a porous tissue chamber wall 816, the inner boundary layer channel 820 can be defined by the porous tissue chamber wall 816 and a porous boundary layer wall 826, the outer boundary layer channel 830 can be defined by the porous boundary layer wall 826 and a porous outer conduit wall 836, and the outer conduit layer channel 840 is defined by the porous outer conduit wall 836 and an external wall 802 that is not porous. Here, the porous walls 816, 826, 836 can include a plurality of posts 860 that form the walls with the gaps between the posts 860. The porous walls 816, 826, 836 have one or more posts 860 laterally or radially oriented to form the walls.

In one embodiment, any of the chambers/conduits can include structure posts 850 that can be used to provide structure between top walls and bottom walls. The structure posts 850 can be coupled to a bottom wall, and may be coupled to a top wall when integrated with the side walls. Also, the top wall as a lid can rest on the structure posts 850. The structure posts can be used for cell culture, and can result in a higher cell density for organ simulations. FIG. 3C shows the central chamber 810 as having the posts 850, but it can be devoid of posts. Any of the boundary channels 820, 830 can include the posts 850 or be devoid of posts. The outer channel 840 can include the posts 850 or be devoid of posts.

The device having the internal chamber surrounded by the capillary channels accurately reproduces the size and flow of a biological microenvironment, and enables a more physiologically-relevant testing system for therapeutic screening, as well as basic research of ischemia and hypoxia. Advantages in microfluidic technology (e.g., polydimethylsiloxane or PDMS based device) enable creation of small volume, inexpensive, disposable chips having the internal chamber surrounded by the capillary channels. Very thin (e.g., <100 μm) PDMS constructs can be used to realize long-term cell culture and cellular assays on these microfluidic chips. In one example, by bonding the polymer microchannel to a custom glass bottom laid out in the appropriate form, the model can be readily extended onto standard well plates (e.g., 24 well plates), providing a ready method to scale-up to high-throughput screening. The device configuration provides the ability to study differences between healthy and diseased microvasculature of the cells (e.g., myocytes).

In one embodiment, the device can provide a microenvironment (e.g., size, volume, and vasculature) of the cells (e.g., cardiomyocytes) with a network of endothelial cells in the capillary channels surrounding the cells in the internal chamber. The devices configuration allows perfusion, occlusion, and reperfusion at the flow rates observed in live capillaries by application to the channels of the device. The device configuration allows introduction of various insults, chemical (e.g., test pharmaceuticals) or physical (e.g., ischemia and hypoxia) to the cells in the capillary channels and internal chamber. The devices, when made from a transparent material or other optically transmissive material, allows for real-time visualization of the assays. The device is amenable to high throughput for therapeutic screening assays for agents to treat ischemia and hypoxia.

Figure 4:
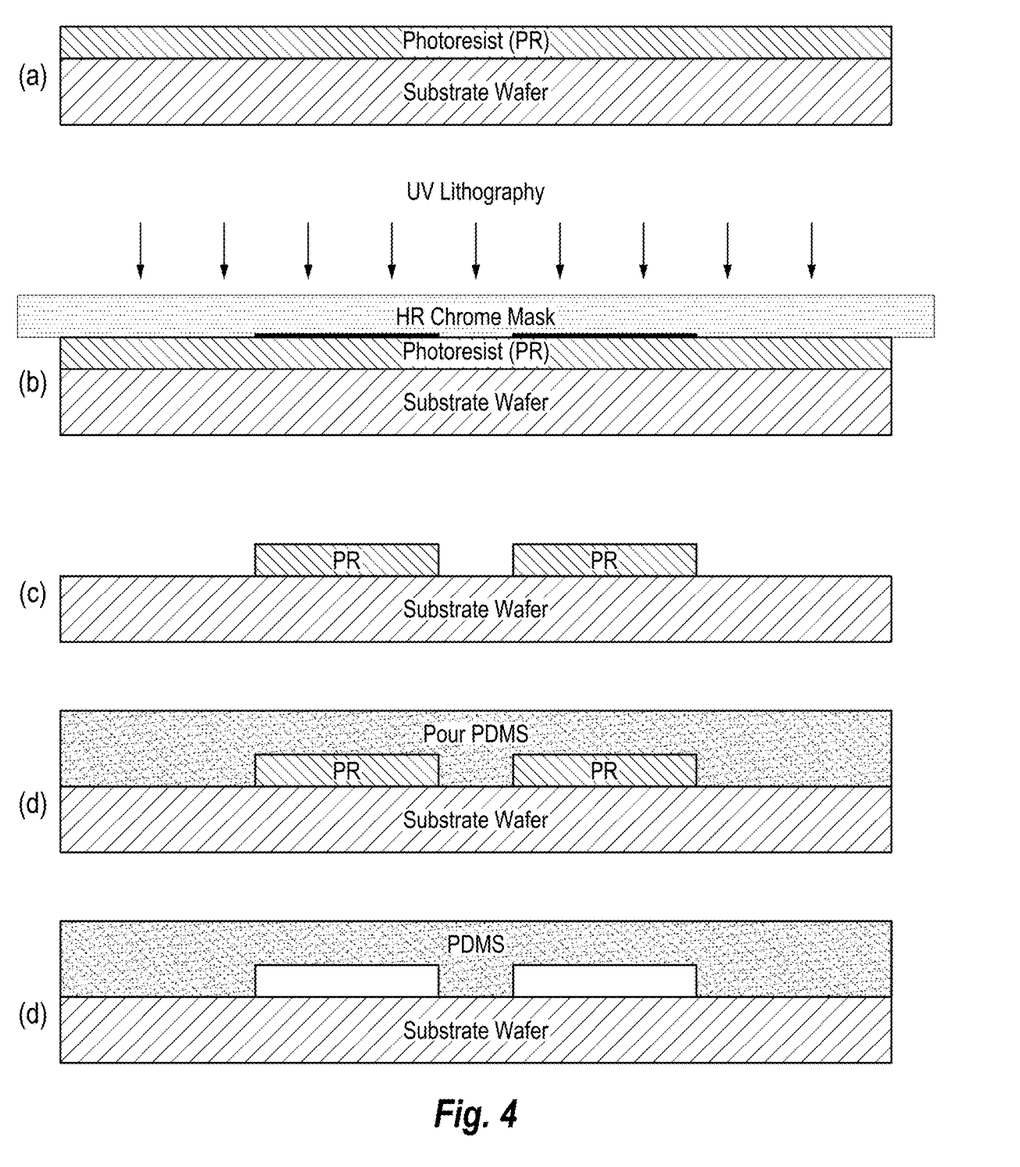
FIG. 4 illustrates an embodiment of manufacturing the device.

The device can be fabricated with PDMS using conventional soft lithography (see FIG. 4). CAD drawings of the device can be developed to include post structures with gaps to act as paths for diffusion of fluid (e.g., nutrients or oxygen) into the central cell chamber. The CAD drawings can also be converted into a computational domain for simulational analysis. Briefly, the steps involved in the fabrication process shown in FIG. 4 include: (a) Spin-coating of photoresist (PR); (b) UV photolithography of the PR; (c) Development of the PR; (d) PDMS casting over developed PR, followed by PDMS curing; and (e) PDMS bonding to a cap (e.g., microscope slides, coverslip, glass, etc.). The devices can be tested visually for structural and fluidic integrity using fluorescent dyes. Fabrication of microfluidic devices from PDMS can be modulated to vary the widths, depths, PDMS concentration and baking time.

Additional methods can be used for preparing the devices, such as the following example. The AutoCAD designs can be printed at high resolution on high-quality chrome masks. The chrome masks can be used for UV patterning of the desired thickness of positive resist spun on top of a silicon wafer. Silanization via the use of an adhesion promoter (Hexamethyldisilazane, HMDS) can be used to enhance the strength of bonding of the photoresist to the silicon wafer. Sylgard 184 PDMS (Dow Corning, Midland, Mich.) can be poured over developed photoresist to generate complementary microchannels in PDMS. The PDMS can be cured at 60° C. for 4-6 hours in an oven, following which the PDMS will be peeled off from the master. Through holes, defining the inlets and outlets, can be punched using a beveled 25-gauge needle. The bonding surfaces of the PDMS and a pre-cleaned (ultrasonicated) glass slide/wafer can be bonded following oxygen plasma treatment. Tygon Microbore tubing with an outside diameter of 0.03" and inner diameter of 0.01" connected to 30 gauge stainless steel needle can be used for world-to-chip interfacing. The completed device can be sterilized by autoclaving at 121° C. for 15 minutes and stored in sterile environment until usage. The finished devices can be tested visually for structural integrity, particularly paying attention to the post structures. The fluidic integrity of the ports and PDMS/glass slide seal can be verified at the operational flow rates.

Various devices configurations can be obtained in accordance with the invention, with central chamber size ranging from 100 μm to 10 mm, surrounded by capillary channels of width 5 μm to 500 μm and height 5 μm to 500 μm, separated by posts 5 μm to 500 μm with gaps of 500 nm to 50 μm. In one example, the device can include a 1 mm central chamber (across) surrounded by 20 μm capillary channels (wide) with a depth of 100 μm (height of chamber and channels). The posts separating the chamber from the capillary channels can be 50 μm wide with gaps of 1 μm. FIG. 6 shows an SEM image of two channels joined by ~50 μm long slits fabricated in our laboratory with PDMS using conventional soft lithography techniques. Also, the gaps can be up to 500 nm. By comparing the yield and performance of different gap sizes in devices, tradeoffs between gap size and performance of ischemia, hypoxia, and myocardial infarct can be studied in these devices.

In one embodiment, in vitro microfluidic devices can be used to assay for analysis of MI or other conditions from ischemia and hypoxia. The MI device can include a plastic disposable and optically clear microfluidic chip with myocytes fed by an array of capillaries comprising of endothelial cells. Synchronized contraction of healthy myocytes can be visualized real-time. Ischemia and hypoxia of varying intensity and duration can be modeled as needed. Effect of both drug based therapies and recent advances in stem cell therapy can be readily tested in the device. The assay can be interfaced with 12-96 well plates (e.g., 24 well plates) for medium to high throughput assays, thereby allowing lower reagent cost, rapid turnaround times and increased biochemical knowledge to yield benefits during therapies. The device can also be used to study targeted therapy for regeneration of myocytes.

The device can include of a microfluidic chip with tissue cells (e.g., myocytes, neurons, hepatocytes, etc.) fed by an array of capillaries comprising of vascular cells (endothelial cells). Perfusion of tissue cells in the central chamber can be varied in intensity and duration by changes in the flow rate in the capillaries. The benefits of the device that can have varied flow in the channels includes: allow perfusion, occlusion and reperfusion at the rates observed in blood vessels; allow introduction of various insults (chemical or physical); provide real-time visualization; and perform medium to high throughput for therapeutic screening assays. This allows the use of the device to range from pharmaceutical companies developing drugs for diseases under ischemia and hypoxia, characterize the mechanisms of ischemia and hypoxia to resolve the individual stimuli, and in drug discovery for the development of regenerative medicine. The device can be used in methods for creating ischemia induced hypoxia. The device can be used in methods for creating reperfusion injury. The device can be used in methods for creating gradients of hypoxia. The device can be idealized, or imaged with vascular and tissue spaces separated by nano to micro gaps. The device can be used in an assay for creation of ischemia induced hypoxia for cells, such as myocytes, neurons, nephrons, or hepatocytes. The device can be used in an assay for ischemia induced hypoxia with co-culture of cells. The device can be used in an assay to screen for chemical based ischemia. The device can be used in an assay for physical (e.g., mechanical stress) means based ischemia. The device can be used in an assay to screen for therapeutics on hypoxic cells.

The device can be used to characterize key components (e.g., viability, pH/hypoxia, biomarkers) in ischemia, hypoxia, and post MI using morphological analysis and fluorescent probes.

The device design parameters (e.g., chamber size, capillary perfusion rates and time points) can be optimized from in vivo data followed by co-culture with endothelial cells. Inflammation based injury following ischemia involving leukocyte interactions can also be demonstrated. The device can be integrated to a well plate format to permit higher throughput. The device can be used in methods to study stem cell therapies for regeneration of the cells (e.g., myocytes) in the central chamber. The device can be used in methods to study drug based therapeutics for cells in the central chamber. Device predictions can be compared with in vivo studies.

A well-controlled system such as the device can enable both drug discovery and basic understanding of the phenomena during and post MI. In addition, use of an in vitro model that mimics the physiological microenvironment of the myocardium can reduce animal studies during the preliminary stages of the therapeutic development. Thus, the device can reproduce the critical biological characteristics of the MI, thereby providing a valid and cost-effective tool for studying new therapeutic approaches.

The invention can provide a microfluidic device that mimics the microenvironment of myocytes in a complex network of capillaries. Fluid flow (blood flow) in these capillaries can be readily switched on and off to simulate ischemia induced conditions. Culture of endothelial cells in capillaries beside the myocardium chamber (myocytes) enables studies on interaction between endothelial cells. The device can include a plastic, disposable and optically clear microfluidic chip containing two distinct sections; a central chamber for culture of myocytes surrounded by capillaries of endothelial cells. The device is created by separating the central chamber for culture of myocytes from the capillary channels lined with endothelial cells by a design utilizing large posts. The posts create islands which are separated by submicron-micron gaps to ensure diffusion based fluidic connection between the capillary channels and the central myocyte chamber leading to a microenvironment observed in vivo with myocytes being surrounded by capillaries.

The device can include a reproduction of complex microvascular networks onto plastic (e.g., PDMS) substrates. These networks, originally rendered from in vivo images of tissues, allow quantitative study of drug particle adhesion to and transfection of vascular endothelial cells in circumstances closely mimicking in vivo conditions. This methodology was used to create devices from a microvascular network of hamster cremaster muscle in vivo ranging from 15-100 μm. FIG. 2A shows an example of the complete microvascular network on the microfluidic chip with a magnified view of microchannels in FIG. 2B.

The device can provide a microenvironment of the cardiomyocytes nourished by a complex network of capillaries and interactions with endothelial cells. The ischemic insult used in the methodologies of the invention allows for studies on reperfusion effects which are strongly implicated in the generation post infarction complications. The device can selectively provide for normal and reduced blood flow situations found in the infarctions. The device allows introduction of both chemical and physical insults to the cells.

In one embodiment, a cell culture device can include: an internal chamber 110 configured for an internal cell culture that has at least one port (e.g., flow inlet 112 and flow outlet 114) coupled to a perfusion modulating device 900 capable of modulating perfusion in the internal chamber 110; at least one fluid channel (e.g., capillary channel 120) bordering the internal chamber 100 that is configured for a channel cell culture that has at least one port (e.g., capillary inlet 122 and capillary outlet 124) coupled to a perfusion modulating device 900a capable of modulating perfusion in the fluid channel; and a wall (e.g., posts 130 and gaps 132) separating the internal chamber 110 and at least one fluid channel having gaps 132 that fluidly couple the internal chamber 110 with the at least one fluid channel, wherein the perfusion modulating device 900a causes reduced fluid flow. In one aspect, the perfusion modulating device 900, 900a includes a pump 902 (see FIG. 1A). In one aspect, the internal chamber 110 includes a first cell type and the at least one fluid channel includes a second cell type. In one aspect, the first cell type has an ischemic zone in the middle, a non-ischemic zone adjacent with the at least one fluid channel, and a border zone between the ischemic zone and non-ischemic zone. In one aspect, the internal chamber 110 and at least one fluid channel are modeled from physiological features. In one aspect, the internal chamber 110 and at least one fluid channel are modeled from idealized features.

In one embodiment, a cell culture system can include: the device of one of the embodiments; and a perfusion modulating device coupled to the port of the internal chamber and/or to the port of the at least one fluidic channel.

In one embodiment, a method of inducing ischemia can include: providing the device of one of the embodiments having a first cell culture in the internal chamber and a second cell culture in the at least one fluid channel; modulating perfusion in the internal chamber with the perfusion modulating device; and assaying for ischemia in the first cell culture. In one aspect, the method can include modulating perfusion in the at least one fluid channel. In one aspect, the method can include varying intensity and duration of fluid flow in the at least one fluid channel so as to vary perfusion in the internal chamber. In one aspect, the method can include introducing a chemical and/or physical insult to the first cell culture in the internal chamber. In one aspect, the method can include inducing gradients of hypoxia in the internal chamber. In one aspect, the method can include inducing hypoxia in myocytes, neurons, nephrons, or hepatocytes in the internal chamber. In one embodiment, the method can include screening therapeutics on hypoxic cells in the first cell culture in the internal chamber. In one embodiment, the method can include characterizing viability, pH, hypoxia, or biomarkers in cells in the first cell culture in the internal chamber. In one embodiment, the method can include regenerating cells the internal chamber. In one embodiment, the method can include visualizing cells in the first cell culture in the internal chamber. In one embodiment, the method can include simulating a myocardial infarct in the first cell culture of myocytes in the internal chamber. In one embodiment, the method can include inhibiting fluid flow in the internal chamber sufficient to induce low to moderate ischemia. In one embodiment, the method can include inhibiting fluid flow in the internal chamber and at least one fluid channel sufficient to induced moderate to severe ischemia.

EXPERIMENTAL

A component useful for mimicking the microenvironment of myocytes is to recreate the 3D matrix conditions found in vivo. In this context the device can use Matrigel in the myocyte chamber to create a 3D Matrix. Cardiac myocytes (e.g. from Lonza, Walkersville, Md.) can be cultured in cell culture medium. A Matrigel (Kleinman & Martin, 2005) solution can be introduced into the chamber from the inlet port of the chamber using a syringe pump and allowed to polymerize for 2 hours. Myocytes at a concentration of $5 \times 10^5$ cells/ml mixed with matrigel can be injected into the chamber and incubated at 37° C. and 5% CO2. Flow in the capillaries can be continuous at a shear rate of 15 $sec^{-1}$ to 500 $s^{-1}$. Media can be replaced using the programmable syringe pump (Harvard PHD 2000). Cell viability can be assed using LIVE/DEAD® viability kits (Invitrogen, CA) with green stain indicating healthy cells and red unhealthy and decaying cells.

A wide variety of cells (e.g., endothelial, epithelial, ovarian, breast) can be cultured in the device. However, each cell type may need fine tuning of culture protocols for culture in these devices. Seeding density of the cells in addition concentration of matrigel can be varied to grow a uniform layer. Finally, media replacement time can be optimized to overcome any rapid buildup of waste products from the cells.

Measurement of Synchronized Beating and Contraction of Myocytes:

Beating exhibited by cardiac myocytes can be recorded using microscope connected to a camera. The procedure can be automated using software (e.g. NIKON Elements) to see if the beating of the myocytes is synchronized. The beats per minute can serve as the baseline for subsequent ischemia assays.

In order to access whether myocytes have intact contractile properties, electrodes can be inserted in the ports of the chamber and an electrical signal can be applied. Contraction length and duration can be recorded for the cells to serve as baseline following ischemia. A plot of % of cells exhibiting synchronized beating can be used to analyze experimental observations. The frequency, voltage and pulse duration being used to test the contraction properties can be varied to yield a plot of contraction length for cells.

Myocytes exchange oxygen and nutrients with the blood across the myocyte-capillary boundary. During normal behavior of blood flow, replacement of fresh nutrients keeps the waste products level low, but after an ischemia, it results in a shock to the myocytes. However, a common feature is that in the periphery of the ischemic zone, myocytes still have access to nutrients via capillaries whereas the area away from the capillaries becomes necrotic. The diffusion of the nutrients from the capillary to the center of the ischemic area is dependent on the consumption rate of the myocytes and the diffusion rate. In order to assess this diffusion the device can perform the following simulation and experiments.

Ischemic conditions can be subsequently generated in the device followed by experimental analysis on pH/hypoxia changes. The device can be used to assay ischemic myocytes using hypoxia markers; pimonidazole and HIF-1alpha; mitochondria depolarization using Mitotracker probe; inflammation using ICAM-1 and P-selectin; and finally for apoptotic regions using Tunnel and Caspase assays. The device can allow monitoring of the gradients for hypoxia regions using SNARF assays. In all experiments, the nucleus can be counterstained with Hoechst to monitor integrity of the cells. LIVE/DEAD® assay can be utilized as needed. A general-purpose Computational Fluid Dynamics (CFD) code (e.g., CFD-ACE+), based on the Finite Volume Method (FVM) can be used to discretize and solve the governing equations for fluid flow and diffusion in the device. A three-dimensional computational mesh similar to the one shown in FIG. 5 can be generated by importing the AUTO-CAD layouts into CFD-GEOM, the grid generation module. The computation-ready geometry and meshes arc then loaded into CFD-ACE+ for simulation. Modules of fluid flow and chemistry can be used. Flow rates mimicking the shear rates observed in capillaries during healthy and ischemic conditions can be simulated. The time taken for the cell culture medium to diffuse through the entire central chamber can be analyzed. Plot of diffusion time versus flow rate can be generated which can provide guidance during the experimental analysis following ischemic, hypoxia, and MI.

Experimental Diffusion in the Myocyte Chamber:

The myocyte chamber and the capillary channels can be primed with phosphate buffer. Fluorescent dye, FITC at a concentration of 1 µM can be injected into the capillary sections of the network. The diffusion rate of FITC from the capillary channels into the myocyte chamber can be recorded by taking time-lapse images of the device every 5 minutes till the chambers are completely filled. A second experiment can be run mimicking the ischemic condition. If the results between the experiments and simulation match well, one can use subsequent simulation runs as guidance for testing any new flow rates.

Modeling MI in the Developed Device:

A MI model can be provided in the device by ischemic shock for the myocytes. This assay can represent the scenario where blood flow (e.g., nutrients and oxygen) is hindered to the myocardium. Reperfusion can be started and the damage to the cardiac myocytes will be assessed. Changes in pH, upregulation of inflammation markers and viability can be measured.

Myocytes exchange oxygen and nutrients with the blood across the myocyte-capillary boundary. In the device, myocytes are initially fed by media replacement through the myocyte-capillary interface and the myocyte chamber itself. During normal behavior of blood flow, replacement of fresh nutrients keeps the waste products level low, but after ischemia, when the supply is limited due to reduced blood flow, it results in ischemic shock in the myocytes. However, a common feature observed in MI hearts is that in the periphery of the infarct, the myocytes still have access to nutrients via capillaries whereas the area away from the capillaries becomes necrotic. The diffusion of the nutrients from the capillary to the center of the infarct area is dependent on the rate of consumption by the myocytes and the diffusion rate. In order to assess this diffusion one can perform the simulations and experiments described herein.

Initiation of Ischemic Shock in the Device:

Myocytes can be allowed to grow to confluence in the myocyte chamber to 80-90% confluency and synchronized beating. A this stage, media perfusion to the myocyte chamber can be stopped completely for 5 minutes, 30 minutes, 4 hours and 24 hours, respectively, to model ischemia and hypoxia. Two different conditions can be utilized. In the first, flow in the capillary channels can be continued (e.g., mimicking low ischemic conditions) during the period of media stoppage to the myocyte chamber. In the second set, flow in the capillary channels can also be stopped (e.g., severe ischemic conditions) for the duration of the blockage and switched back on at the respective time points. At respective end time points, cell conditions can be assayed for synchronized beating, intact contraction and viability. Control experiments with flow being normal in both the myocyte chamber and capillary channels can be performed. A plot of distance versus cells with synchronized beating from the capillary channel to the center of the chamber can be generated and compared to controls. Similarly, the reduction in the contractile length and the number of cells can be compared. Morphological analysis of the cells can be conducted using phase contrast microscopy.

Three distinct regions of ischemia can be induced as shown in FIG. 1A; (a) the ischemic zone where the cells don't have access to fresh media and waste metabolites are present in excess specifically for the cells present in the center of the chamber, (b) the border zone where partial cells experience excess waste metabolites and hypoxia whereas the other half of cells are viable, and finally (c) non-ischemic zone, where the cells have abundant supply of fresh nutrients near to the capillary channels.

An example of a method of creating hypoxia is shown in Table 1.

TABLE 1

Example to create Hypoxia

| Tissue Chamber | Flow in Capillary | Time Point | Condition of Mimicked |
|---|---|---|---|
| Flow On | On (15 sec-1) | 5, 30 minute, 4 and 24 hr | Healthy Cells (Control) |
| Flow Off | On (15 sec-1) | 5, 30 minute, 4 and 24 hr | Low Level Ischemia |
| Flow Off | On (2.5 sec-1) | 5, 30 minute, 4 and 24 hr | Low to moderate Ischemia |
| Flow Off | Off and On (15 sec-1) | 5, 30 minute, 4 and 24 hr | Moderate Ischemia |
| Flow Off | Off and On (2.5 sec-1) | 5, 30 minute, 4 and 24 hr | Severe Ischemia |

The flow in capillary Off and On implies that the flow in capillary channel was also stopped during the stoppage of flow in the central chamber for the respective time points of 5 minutes, 30 minutes, 4 hours and 24 hours. However, at the end of these time points, flow in capillary channel was turned on and the cells were assayed for viability at 24 hour post flow being turned on. This mimics the reperfusion scenario observed in vivo.

One can look at alternative time points for the varying ischemic effects on the myocytes.

Measurement of pH/hypoxia changes in the Myocyte Chamber:

Following ischemia, a gradient of hypoxia can be developed as the nutrients are not being replenished fast enough to the myocytes. This results in pH changes in regions of the myocardium or the myocyte chamber in the device. In order to access the varying pH/hypoxia conditions in the myocyte chamber, one can use the fluorescent pH indicator dye SNARF®-4F (Invitrogen, CA) which exhibits a significant pH-dependent emission shift (from yellow-orange to deep red fluorescence) and allows determination of hypoxic regions. The myocyte chamber can be injected with SNARF-4F at a concentration of 10 µM diluted in cell culture media. The entire chamber can be then divided into sections using virtual grids. Image analysis can be performed to yield areas with varying levels of pH changes by plotting distance from capillary channel versus intensity. The varying pH/hypoxia conditions in the myocyte chamber can be determined.

Pimonidazole Based Measurements:

Hypoxic cells in the co-culture can be detected using the Hypoxyprobe-1 Plus Kit (NPI Inc) according to the manufacturer's instructions. In brief, cells can be incubated with pimonidazole (400 µM) for 2 hr followed by fixation using 4% formaldehyde and permeabilized using 0.1% Triton X-100. After blocking with BSA, cells can be labeled with Hypoxyprobe Mab 1-FITC (1:200). Nuclei will be stained with Hoechst followed by fluorescence imaging.

pH Indicator Dye Based Measurements:

SNARF®-4F (Invitrogen, CA) which exhibits a significant pH-dependent emission shift (from yellow-orange to deep red fluorescence) allows determination of hypoxic regions. The myocyte chamber can be injected with SNARF-4F (10 µM) and the resultant fluorescent intensity can be imaged.

The concentration of SNARF®-4F used (10 µM) is typical for monitoring pH gradients. However, in case the intensity levels are indistinguishable between the varying regions of the myocyte chamber, concentrations can be dropped or increased to get better signal to noise ratio of the pH gradients. Other SNARF dyes such as SNARF-1 and SNARF-5 can be utilized as needed.

Data can be measured by generation of a plot showing distinct gradients of hypoxia (pH changes) from the capillary channel to the center of the myocyte chamber. A three zone differential pattern of ischemia is expected with significant variations in the patterns following a low ischemia induced MI to a critical ischemia induced MI.

Biomarker Analysis in the Myocyte Chamber:

It is known that certain adhesion molecules such as ICAM-1 and P selectin are upregulated following MI on the myocytes. In addition, hypoxia-inducible factor-1 (HIF-1) is known to be upregulated in myocytes following hypoxic conditions. At regular time points of the ischemia experiments (Table 1), cells can be incubated with fluorescently tagged antibodies to ICAM-1 and HIF-1. The entire chamber can be divided into virtual grids to yield areas with differential expression of these markers. The location of these markers on the cells can be compared with the hypoxic regions from the SNARF assay to validate the zones of ischemia and the levels of biomarkers.

One can use antibodies to adhesion molecules (e.g. ICAM-1) to assess the % of cells expressing the inflammation marker and their location in the entire chamber. 2 µm fluorescent microspheres (Polysciences Inc., Warrington, Pa.) at a concentration of $2 \times 10^8$ particles/ml can be coated with anti-ICAM-1 (BD Biosciences, San Jose, Calif.). Microspheres washed 2× in 0.1 M NaHCO3 buffer pH 9.2 can be incubated with Protein A (Zymed, Carlsbad, Calif.) at a concentration of 300 µg/ml and incubated at room temperature overnight to saturate the surface of the microsphere. The following day, a 2× wash with solution containing 1% BSA in HBSS can be performed. The microspheres can be resuspended in 1% BSA in HBSS and incubated at room temperature for 20 minutes. Following incubation and subsequent 2× wash with buffer, anti-ICAM-1 antibody at a concentration of 100 µg/ml diluted in 1% BSA/HBSS can be mixed with the microspheres. Protein A binds the Fc fragment of the antibody to allow proper orientation of the antibody. The microspheres can be held in this solution at 4° C. until experimentation. Prior to experiments, microspheres can be washed twice with 1% BSA and HBSS. A control set of microspheres with IgG coating can also be prepared. The prepared particles can be injected into the myocyte chamber diluted in cell culture media to a concentration of $10^6$ particles/ml at the time point showing maximum MI. Following incubation period (e.g., 30 minutes), a wash can be performed with PBS and the cells will be imaged.

Apoptotic Assays:

Cells under hypoxia are subject to stress eventually leading to apoptosis. Hence, they can be monitored using Tunnel (measurement of nuclear DNA fragmentation), or Caspase (caspase activity in apoptotic cells) assay. Cells can be fixed with 4% paraformaldehyde for 1 hr and permeabilized in 0.1% Triton-100, 0.1% sodium citrate (4° C. for 2 min) followed by incubation with TUNEL reaction mixture (1 hr at 37° C.). After washing, cells can be incubated with alkaline phosphatase-conjugated antibody (30 min at 37° C.) followed by counterstained with hematoxylin. For Caspase assay, the cells can be incubated with the reaction solution (1 hr at 37° C.) followed by a wash and counterstaining with Hoechst dye. We can also use Mitotracker red (stains mitochondria) for determining depolarization of cells following hypoxia.

As before, the chamber can be divided into virtual grids to yield areas with differential expression of the markers. The locations of the fluorescence images can be correlated with the SNARF and pimonidazole images to validate the hypoxia regions and zones of ischemia.

In addition, one can perform gene expression analysis (RT-PCR) to validate the upregulation of the hypoxia and inflammation markers. Finally, one can explore whole genome arrays to identify upregulated genes for the different regimes of ischemia.

Transport Model for Prediction of Hypoxia and Regeneration Following MI:

A morphologically realistic mathematical model of oxygen transport in cardiac tissue following infarction can be used to supplement the experimental studies. The model utilizes microvascular morphology of cardiac tissue based on available morphometric images to simulate experimentally measured oxygen levels after MI. Model simulations of relative oxygenation match experimental measurements closely and can be used to simulate distributions of oxygen concentration in normal and infarcted hearts of rodents. 3,3-diheptyloxacarbocyanine iodide (DiOC7) and CD31 staining can be used to measure the number of anatomic and perfused vessels. Hypoxia levels can be measured by the use of EF5 (a pentafluorinated derivative of etanidazole) that is preferentially metabolized in hypoxia cells.

Viability of Myocytes:

In order to assess the viability and healthy condition of the myocytes in the microfluidic device, one can use a combination of fluorescent dyes. Propidium iodide (Invitrogen, CA), an indicator of membrane leakiness and cell death in combination with SYTO16 (viable cell indicator) are commonly used to assess cell viability. Propidium iodide and SYTO16 at a concentration of 0.5 µg/mL in cell culture medium can be injected into the myocyte chamber. After 15 minutes of incubation, images of the cells can be acquired using epi-fluorescence microscopy. The % of cells showing uptake of propidium iodide (stain in red) can indicate cells not in healthy condition, whereas cells staining with SYTO16 (stain green) indicate healthy cells. This method can be used to ascertain % of viable cells following MI in the device.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations maybe expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

This patent document incorporates by specific reference in their entirety the following patents and patent applications: U.S. Pat. No. 7,725,267; 8,355,876; 8,175,814; 8,380,443; 8,417,465; 8,589,083; U.S. 2010/0227312; PCT/US2013/072081; U.S. 2013/0101991; and U.S. 2013/0149735. These applications provide background and state of the art as well as definitions for terms of art.

This patent document incorporates by specific reference in their entirety co-filed applications that claim priority to the same provisional application 61/775,158 filed Mar. 8, 2013, which co-filed applications include: C1478.10020US02 (authorized to include serial number once known); C1478.10020US03 (authorized to include serial number once known); and C1478.10020US04 (authorized to include serial number once known).

The invention claimed is:

1. A method of inducing ischemia, the method comprising:
providing a cell culture device having a first cell culture in an internal chamber and a second cell culture in at least one fluid channel, the cell culture device comprising:
the internal chamber being configured for an internal cell culture that has at least one port coupled to a perfusion modulating system capable of modulating perfusion of media in the internal chamber;
the at least one fluid channel bordering the internal chamber, the at least one fluid channel being configured for a channel cell culture that has at least one port coupled to the perfusion modulating system capable of modulating perfusion of media in the at least one fluid channel; and
a wall separating the internal chamber and at least one fluid channel having gaps that fluidly couple the internal chamber with the at least one fluid channel, wherein the perfusion modulating system causes changes in oxygen flow in the internal chamber and/or at least one fluid channel;
flowing liquid media having oxygen through the internal chamber and at least one fluid channel of the cell culture device;
modulating oxygen perfusion in the internal chamber with the perfusion modulating system by varying and selectively blocking the flow rate of at least one of the liquid media or oxygen through the internal chamber to induce varying levels of ischemia; and
assaying for ischemia in the first cell culture.

2. The method of claim 1, comprising modulating oxygen perfusion in the at least one fluid channel.

3. The method of claim 1, comprising varying flow rate and duration of fluid flow of the liquid media or oxygen in the at least one fluid channel so as to vary perfusion of oxygen in the internal chamber.

4. The method of claim 1, comprising introducing a chemical, biological and/or physical insult to the first cell culture in the internal chamber.

5. The method of claim 1, comprising inducing a gradient of hypoxia in the internal chamber.

6. The method of claim 1, comprising inducing hypoxia in tissue cells in the internal chamber.

7. The method of claim 1, comprising screening therapeutics on hypoxic cells in the first cell culture in the internal chamber.

8. The method of claim 1, comprising characterizing viability, pH, hypoxia, or biomarkers in cells in the first cell culture in the internal chamber.

9. The method of claim 1, comprising regenerating cells in the internal chamber.

10. The method of claim 1, comprising visualizing cells in the first cell culture in the internal chamber.

11. The method of claim 1, comprising simulating a myocardial infarct in the first cell culture in the internal chamber, wherein the first cell culture includes myocytes.

12. The method of claim 1, comprising modulating nutrient levels in the internal chamber to induce the varying levels of ischemia.

13. The method of claim 12, comprising modulating nutrient levels in the internal chamber and at least one fluid channel to induce moderate to severe ischemia.

14. The method of claim 1, wherein the perfusion modulating system includes a pump.

15. The method of claim 1, wherein the internal chamber includes a first cell type and the at least one fluid channel includes a second cell type.

16. The method of claim 15, wherein the first cell type has an ischemic zone in the middle, a non-ischemic zone adjacent with the at least one fluid channel, and a border zone between the ischemic zone and non-ischemic zone.

17. The method of claim 1, wherein the internal chamber and at least one fluid channel are modeled from physiological features.

18. The method of claim 1, wherein the internal chamber and at least one fluid channel are modeled from idealized features.

19. The method of claim 1, further comprising selectively blocking flow of the liquid media through the cell culture device in order to block flow of the oxygen through the cell culture device.

* * * * *